(12) United States Patent
Haggins, Jr. et al.

(10) Patent No.: US 10,443,032 B2
(45) Date of Patent: Oct. 15, 2019

(54) DEVICE AND METHOD FOR ISOLATION OF CORNEAL ENDOTHELIAL CELLS

(71) Applicant: THE UNITED STATES OF AMERICA AS REPRESENTED BY THE SECRETARY OF THE ARMY, Fort Detrick, MD (US)

(72) Inventors: Robert Haggins, Jr., Belcamp, MD (US); Erik Eaton, Jr., Havre de Grace, MD (US); Zachary Murray, Jarrettsville, MD (US); Timothy Varney, Baltimore, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 16/060,078
(22) PCT Filed: Apr. 19, 2017
(86) PCT No.: PCT/US2017/028242
§ 371 (c)(1),
(2) Date: Jun. 7, 2018
(87) PCT Pub. No.: WO2017/184667
PCT Pub. Date: Oct. 26, 2017

(65) Prior Publication Data
US 2019/0002818 A1 Jan. 3, 2019

Related U.S. Application Data

(60) Provisional application No. 62/324,476, filed on Apr. 19, 2016.

(51) Int. Cl.
*C12M 3/00* (2006.01)
*C12M 1/00* (2006.01)
(Continued)

(52) U.S. Cl.
CPC ............ *C12M 47/04* (2013.01); *C12M 23/02* (2013.01); *C12M 25/00* (2013.01); *C12M 29/06* (2013.01);
(Continued)

(58) Field of Classification Search
CPC ...... C12M 21/08; C12M 25/06; C12M 23/10; C12N 5/0671; C12N 5/0621; A61F 2/142
See application file for complete search history.

(56) References Cited

U.S. PATENT DOCUMENTS 3,745,091 A 7/1973 McCormick
5,591,636 A * 1/1997 Grass .................... B01D 61/18
324/450

(Continued)

FOREIGN PATENT DOCUMENTS

DE 102014222547 B3 2/2016
EP 280610 A1 11/2014

OTHER PUBLICATIONS

Thiel et al.: "A simple corneal perfusion chamber for drug penetration and toxicity studies", British Journal of Ophtamlmology, vol. 85, No. 4, Apr. 1, 2001 (Apr. 1, 2001), pp. 450-453, XP002772567, figures 1,2.

*Primary Examiner* — Nathan A Bowers
(74) *Attorney, Agent, or Firm* — Elizabeth Arwine; William Eshelman

(57) ABSTRACT

An apparatus (8) for isolating corneal endothelial cells (34) (CECs) includes a base portion (10) having an interior recessed opening (14) with a bottom surface (16). A convex projection (18) is centrally located on the bottom surface (16) and is configured to receive an inverted cornea (32). A top portion (12) is configured to mate with the base portion (10). The top portion (12) includes a fluid chamber (24) with a lower surface (20). The lower surface (20) has an opening (22) therein in which the convex projection (18) projects when the top portion (12) is mated with the base portion (10).

26 Claims, 11 Drawing Sheets

(51) Int. Cl.
*C12M 1/12* (2006.01)
*C12M 1/36* (2006.01)
*C12N 5/071* (2010.01)

(52) U.S. Cl.
CPC ............ *C12M 29/14* (2013.01); *C12M 29/26* (2013.01); *C12M 41/48* (2013.01); *C12N 5/0602* (2013.01)

(56) References Cited

U.S. PATENT DOCUMENTS

| | | | |
|---|---|---|---|
| 5,789,240 A * | 8/1998 | Abdulrazik | G01N 13/00 435/284.1 |
| 6,773,916 B1 * | 8/2004 | Thiel | C07K 16/28 435/326 |
| 7,169,578 B2 | 1/2007 | Wang et al. | |
| 7,371,584 B2 | 5/2008 | Feistel | |
| 7,449,307 B2 * | 11/2008 | Cima | B01L 3/5085 424/449 |
| 7,799,520 B2 | 9/2010 | Ross et al. | |
| 8,309,344 B2 | 11/2012 | Chang et al. | |
| 8,609,408 B2 | 12/2013 | Fan et al. | |
| 2006/0025577 A1 | 2/2006 | Ferrara et al. | |
| 2008/0294149 A1 * | 11/2008 | Krolman | A01N 1/02 606/1 |
| 2014/0170751 A1 | 6/2014 | Hayashi et al. | |
| 2014/0357511 A1 | 12/2014 | Handique et al. | |
| 2015/0168278 A1 | 6/2015 | Hale | |
| 2016/0008408 A1 | 1/2016 | Imagawa et al. | |
| 2016/0029618 A1 | 2/2016 | Gain et al. | |

* cited by examiner

US 10,443,032 B2

DEVICE AND METHOD FOR ISOLATION OF CORNEAL ENDOTHELIAL CELLS

STATEMENT OF GOVERNMENT INTEREST

The invention described herein may be manufactured, used and licensed by or for the United States Government.

BACKGROUND OF THE INVENTION

The invention relates in general to the isolation of certain types of animal cells and in particular to the isolation of specific types of cells found in the eye.

FIG. 8 is a side sectional view of a human eye 28. The eye 28 has a lens 30 and a cornea 32. FIG. 9 is an enlarged sectional view of the cornea 32. Mammalian conical endothelial cells (CECs) 34 are a single layer of cells located on the posterior side of the cornea 32, facing the anterior chamber. The outermost layer of the cornea 34 is the epithelium 36. CECs 34 allow nutrients from the anterior chamber to pass into the cornea 32. CECs 34 pump water out of the cornea 32 and into the anterior chamber. CECs 34 in the intact adult human eye have limited growth potential. CECs demonstrate highly limited growth potential in vivo. A reduction in CEC number is normally observed during aging, but this is usually accommodated for by an increase in average cell diameter.

If a critical number of CECs are lost due to disease or injury, this compensatory response is no longer sufficient, and the endothelial barrier is breached. Subsequent corneal edema results in significant inflammation, epithelial bullae, and limbal stem cell deficiency. Together these complications can eventually lead to corneal opacity and total vision loss. The best characterized examples of CEC loss include Fuch's dystrophy (a genetically-based degenerative disease of the corneal endothelium), aphakic/pseudophakic bullous keratopathy (PBK, resulting from endothelial cell injury incurred during cataract surgery) and mustard gas keratopathy (MGK, which occurs following ocular exposure to the chemical warfare agent sulfur mustard). Surgical intervention by corneal transplant is the only currently available option for patients with critical CEC loss. However, transplantation is often unavailable due to the limited supply of fresh corneas suitable for transplantation. Patients that do receive donated tissue face the possibility of transplant rejection.

A known process for isolating CECs is called Descemet's stripping. This procedure involves the use of a sharp, bladed instrument known as a trephine. The trephine is used to scrape CECs 34 away from the underlying basement membrane 38 (Descemet's Membrane). This method can frequently result in the co-isolation of corneal stromal cells 40 (keratocytes) located beneath Descemet's Membrane 38. Keratocytes 40 have a very high proliferative potential. Therefore, CEC isolation by Decemet's stripping often results in the overgrowth of contaminative keratocytes 40 during cell culture expansion, rendering the expanded cells unusable for transplant or for the study of a homogenous CEC population.

A need exists for an apparatus and method for isolating pure populations of CECs from a cornea.

SUMMARY OF THE INVENTION

A first aspect of the invention is an apparatus for isolating conical endothelial cells (CECs). The apparatus includes a base portion having an interior recessed opening with a bottom surface. A convex projection is centrally located on the bottom surface and configured to receive an inverted cornea. A top portion is configured to mate with the base portion. The top portion includes a fluid chamber with a lower surface. The lower surface has a central opening therein in which the convex projection projects when the top portion is mated with the base portion. The lower surface of the top portion extends from and angles up and away from the opening therein and joins a side wall of the top portion. The inverted cornea forms a fluid seal between the fluid chamber of the top portion and the interior recessed opening of the base portion. Only the endothelial surface of the inverted cornea is exposed to the fluid chamber.

The angle between the lower surface of the top portion and the horizontal may be in a range of 30 degrees to 70 degrees. More preferably, the angle is in a range of about 40 degrees to about 60 degrees.

The apparatus may include a groove formed on the lower exterior circumferential surface of the top portion and an O-ring disposed in the groove. The O-ring provides a friction fit between the top portion and the base portion.

The apparatus may include a plurality of the top portions wherein the opening in each top portion has a different diameter.

The apparatus may be configured for printing by a 3D printer.

Another aspect of the invention is a method for isolating corneal endothelial cells (CECs). The method may include providing the apparatus of the first aspect of the invention and a cornea, and placing the cornea with its endothelial side up over the convex projection. The top portion is then mated with the base portion such that the convex projection extends into the opening and an endothelial layer of the cornea contacts an entire circumference of the opening. Only the endothelial layer is exposed to the fluid chamber of the top portion.

A further aspect of the invention is an assembly including a reservoir containing a reagent and a peristaltic pump fluidly connected to the reservoir with tubing. A microcontroller is connected to and in control of the peristaltic pump. The assembly may include the apparatus of the first aspect of the invention. The fluid chamber is connected to the peristaltic pump with the tubing. A lid closes the top portion and a spray nozzle is fixed to the lid. The nozzle is configured to receive the reagent from the tubing and spray the reagent in the fluid chamber onto the inverted cornea. A collection tube for collecting the reagent and endothelial cells from the fluid chamber is connected to the fluid chamber with a second tubing.

Preferably, the spray nozzle is a full cone spray nozzle.

A second peristaltic pump may be connected to and controlled by the microcontroller and interposed in the second tubing between the fluid chamber and the collection tube. The second tubing extends into the fluid chamber and terminates adjacent to the inverted cornea.

Another aspect of the invention is an assembly having a first reservoir containing a first reagent, a first peristaltic pump fluidly connected to the first reservoir with a first tubing, a second reservoir containing a second reagent, a second peristaltic pump fluidly connected to the second reservoir with a second tubing, and a microcontroller connected to and in control of the first and second peristaltic pumps. The assembly may include the apparatus of the first aspect of the invention. The fluid chamber is connected to the first and second tubing by a Y-connection tubing. A check valve is disposed in each of the first and second tubing upstream from the Y-connection tubing. A lid closes the top portion and a spray nozzle is fixed to the lid. The spray nozzle is configured to receive the first and second reagents from the Y-connection tubing and spray the first and second reagents in the fluid chamber onto the inverted cornea. A collection tube for collecting the first and second reagents and endothelial cells from the fluid chamber is connected to the fluid chamber with a third tubing. A third peristaltic pump is connected to and controlled by the microcontroller and interposed in the third tubing between the fluid chamber and the collection tube.

Preferably, the spray nozzle is a full cone spray nozzle.

The third tubing may extend into the fluid chamber and terminate adjacent to the inverted cornea.

The invention will be better understood, and further objects, features and advantages of the invention will become more apparent from the following description, taken in conjunction with the accompanying drawings.

BRIEF DESCRIPTION OF THE DRAWINGS

In the drawings, which are not necessarily to scale, like or corresponding parts are denoted by like or corresponding reference numerals.

DETAILED DESCRIPTION

When donated corneas are available, CECs may be isolated from the corneas and the number of CECs expanded by in vitro culture. The CECs may then be frozen. The Human Leukocyte Antigen (HLA) profile may be used to determine the immunologic compatibility of the donor for each batch of frozen CECs. Cyro-preserved CEC stocks may then be available for transplant to immunologically compatible patients.

Figure 1:
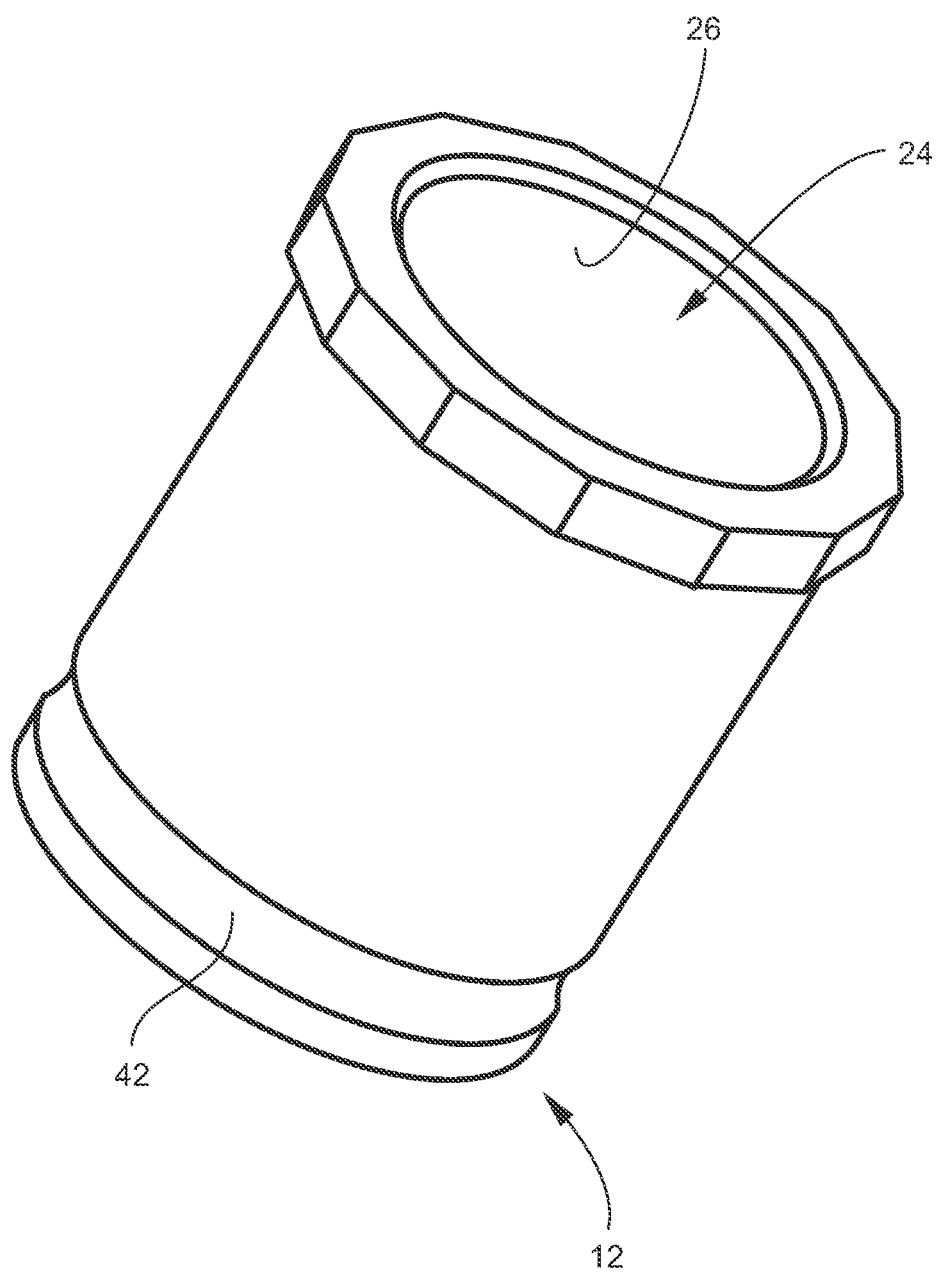
FIG. 1 is a side perspective view of a top portion of one embodiment of a device for isolating CECs.
Figure 2:
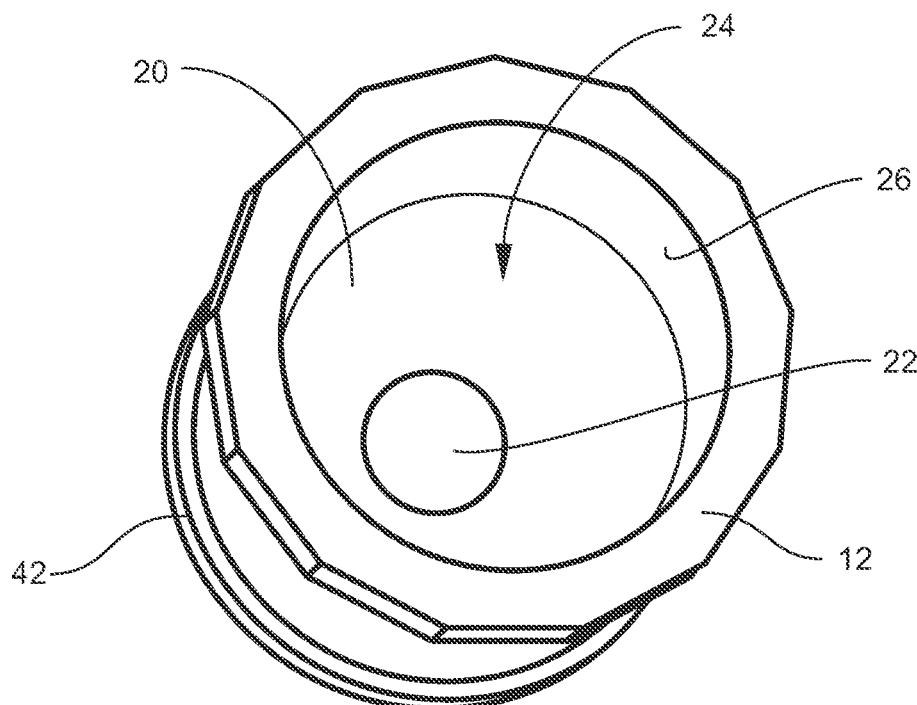
FIG. 2 is a top perspective view of FIG. 1.
Figure 3A:
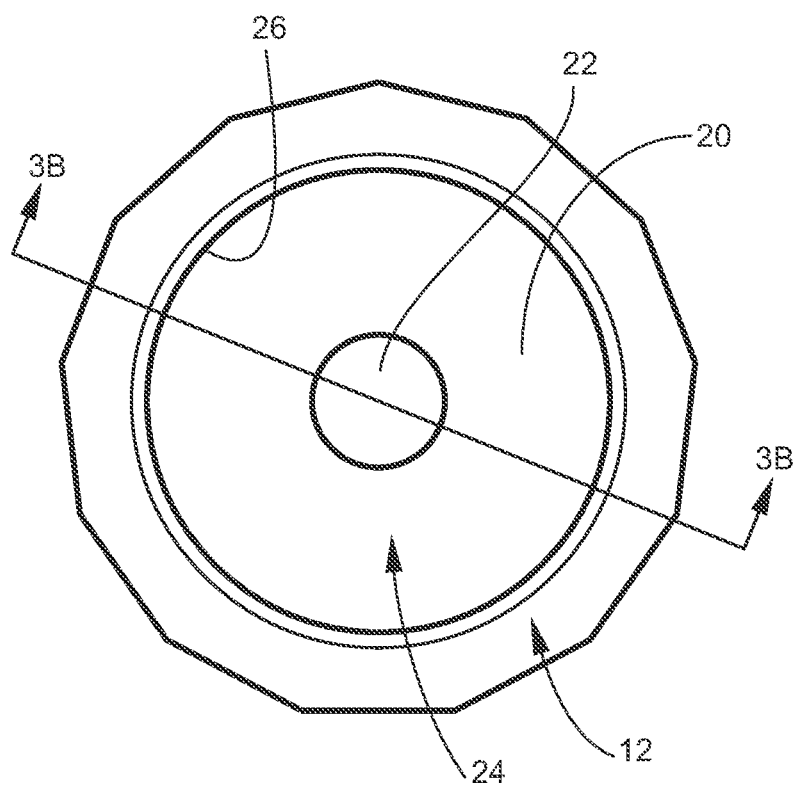
FIG. 3A is a top view of FIG. 1.
Figure 3B:
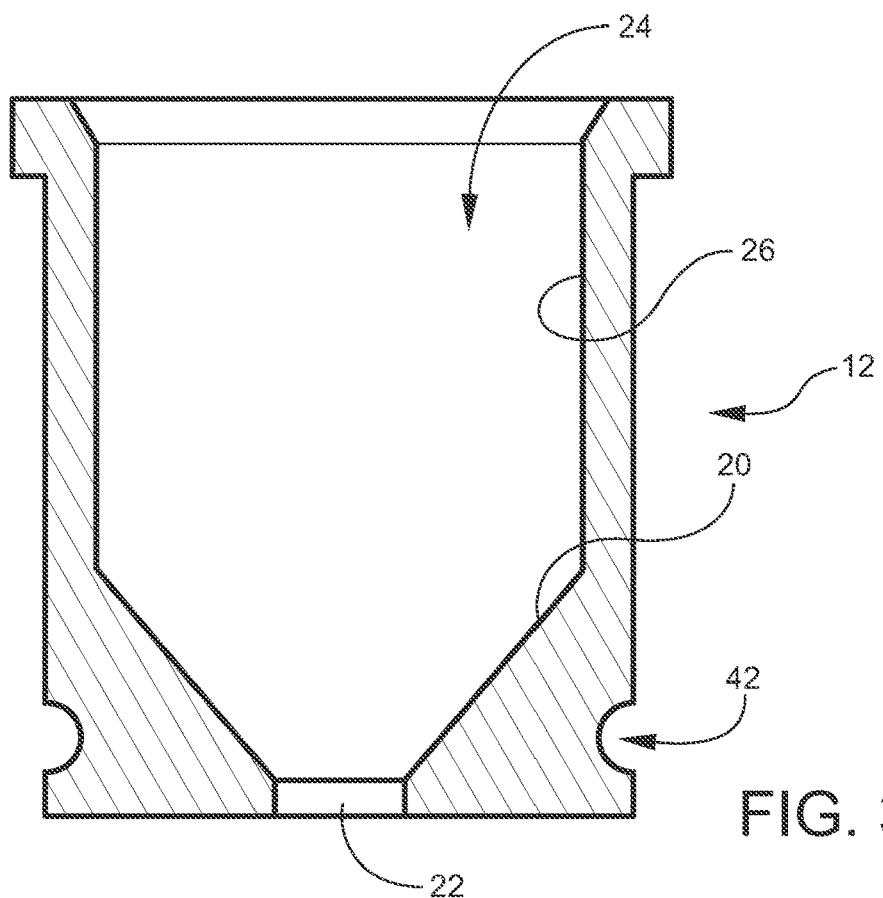
FIG. 3B is a sectional view taken along the line 3B-3B of FIG. 3A.
Figure 4:
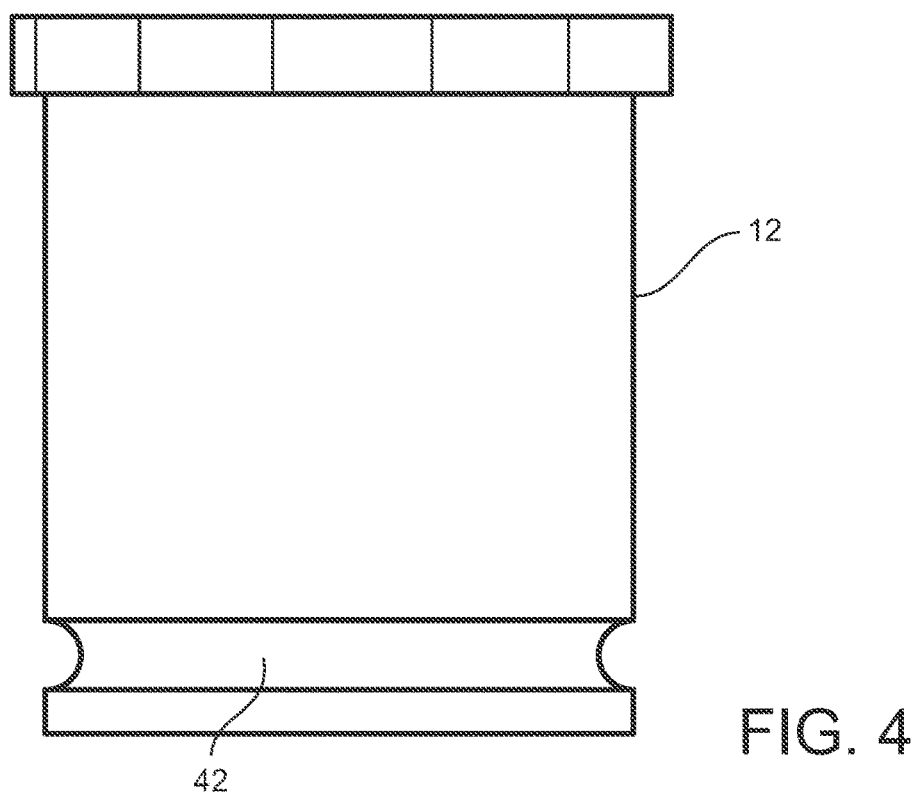
FIG. 4 is a side view of FIG. 1.
Figure 5:
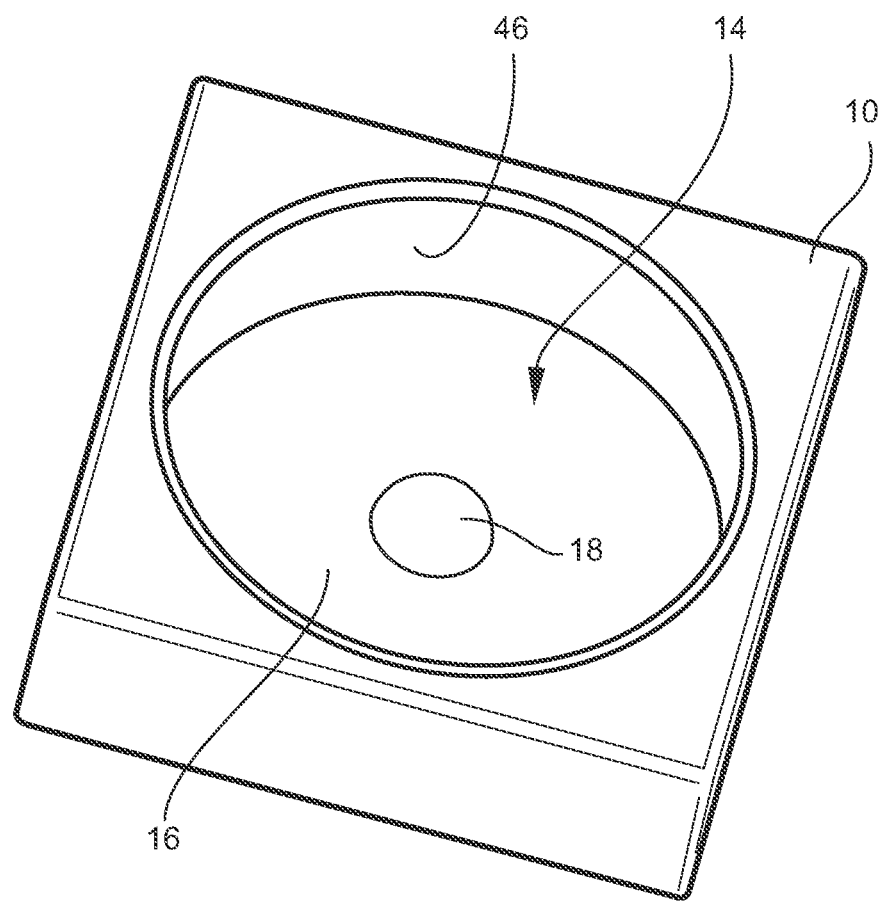
FIG. 5 is a perspective top view of a base portion of one embodiment of a device for isolation CECs.
Figure 6A:
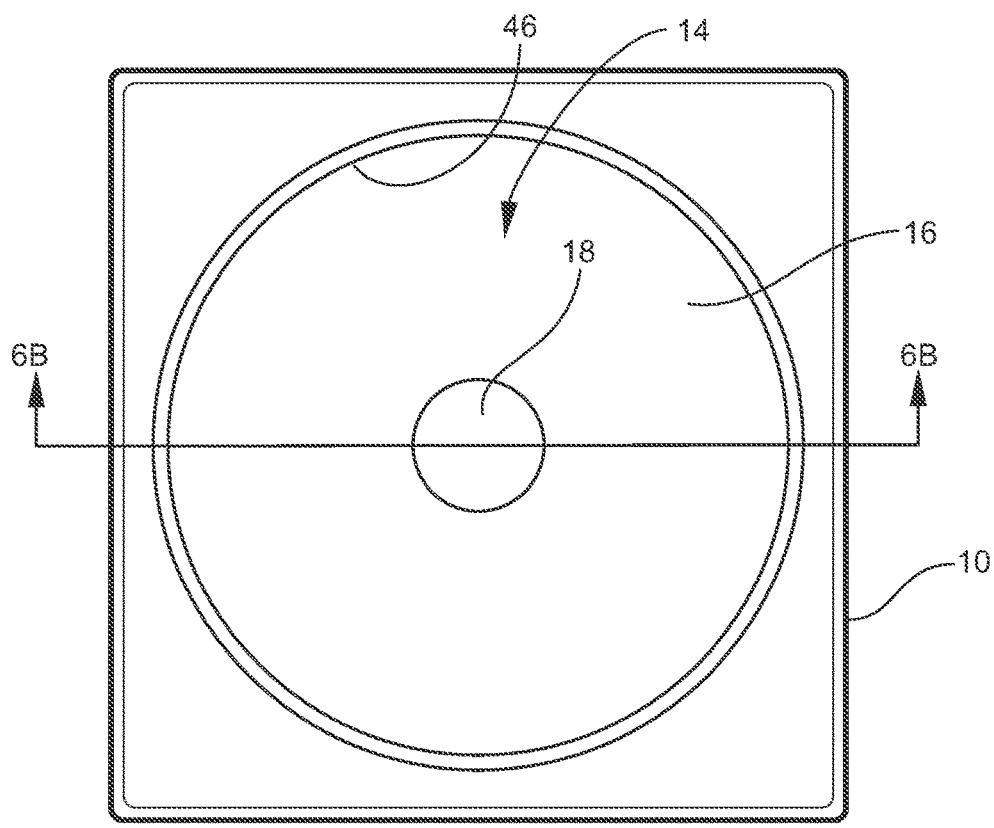
FIG. 6A is a top view of FIG. 5.
Figure 6B:
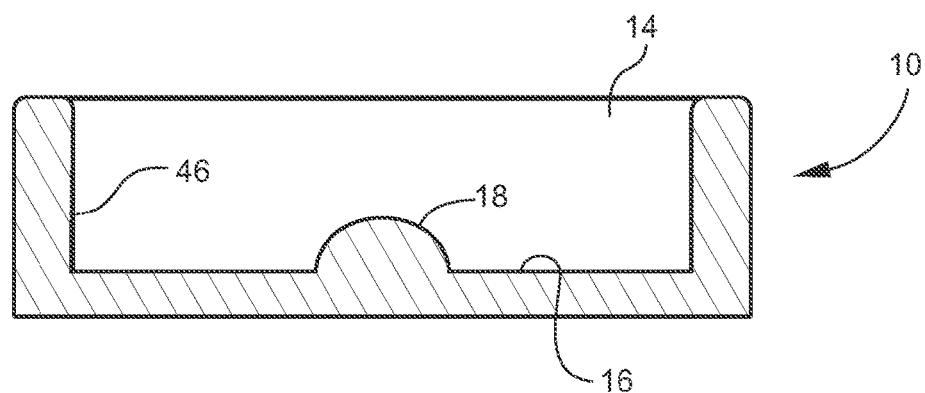
FIG. 6B is a sectional view taken along the line 6B-6B of FIG. 6A.
Figure 7:
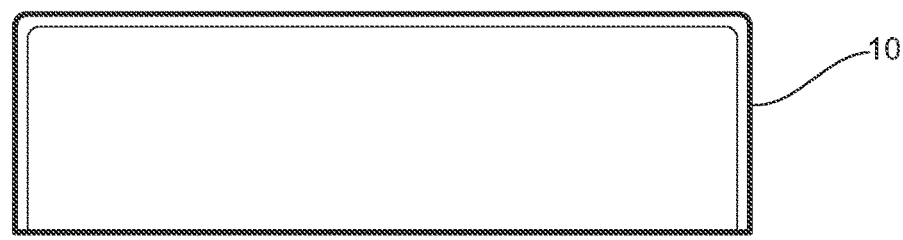
FIG. 7 is a side view of FIG. 5.
Figure 8:
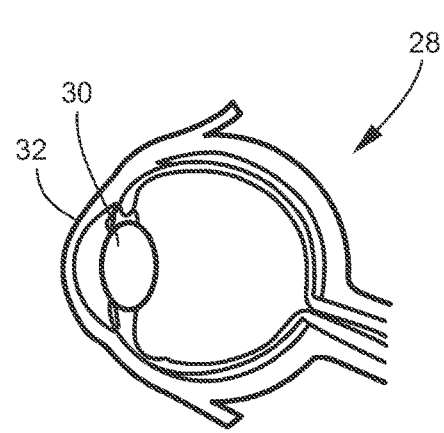
FIG. 8 is a side sectional view of a human eye.
Figure 9:
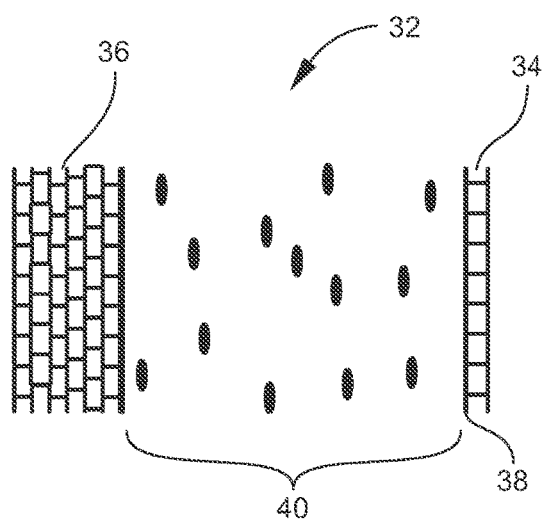
FIG. 9 is an enlarged sectional view of a cornea.

A novel device 8 (FIG. 11) for isolating CECs includes a base portion 10 (FIGS. 5-7) and a top portion 12 (FIGS. 1-4) that fits on the base portion 10. The base portion 10 has an interior recessed opening 14 with a bottom surface 16. A convex projection 18 is centrally located on the bottom surface 16 and configured to receive an inverted cornea 32 (FIGS. 8 and 9). That is, the epithelium 36 is placed in contact with the convex projection 18 so that the endothelium 34 faces upward away from the base portion 10. In this condition, the cornea 32 is in a state of curvature that is opposite its natural state of curvature shown in FIG. 8.

Figure 11:
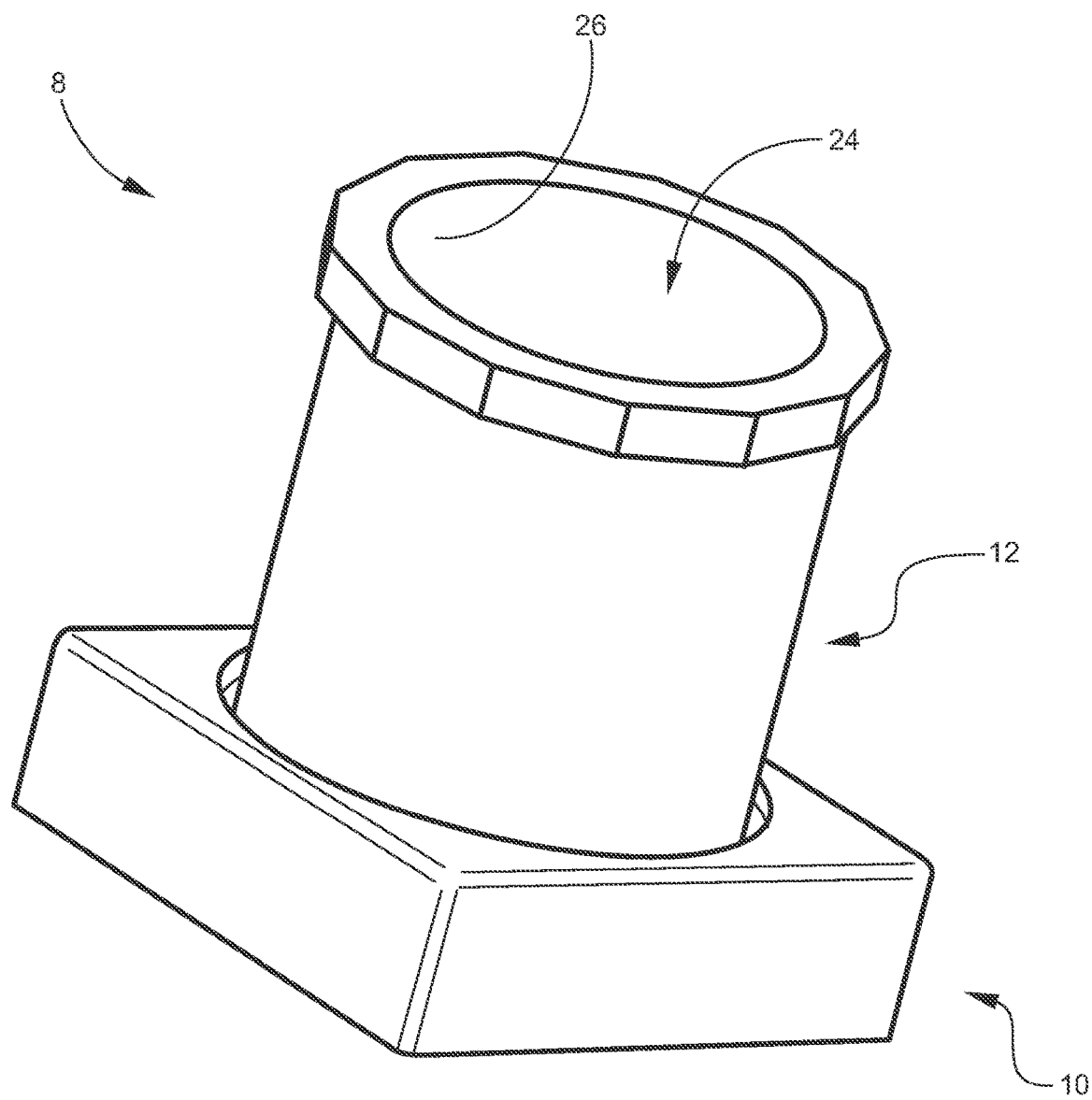
FIG. 11 is a perspective view of an isolation device showing the top portion of FIG. 1 assembled to the base portion of FIG. 5.

The top portion 12 is configured to mate with the base portion 10 (see FIG. 11). The top portion 12 includes a fluid chamber 24 with a lower surface 20. The lower surface 20 has a central opening 22 therein in which the convex projection 18 projects when the top portion 12 is mated with the base portion 10. The lower surface 20 of the top portion 12 extends from and angles up and away from the opening 22 and joins a side wall 26 of the top portion 12. The angle of the lower surface 20 with the horizontal may be in a range of about 30 degrees to about 70 degrees. Preferably, the angle of the lower surface 20 with the horizontal is in a range of about 40 degrees to about 60 degrees. More preferably, the angle is about 50 degrees.

Figure 10:
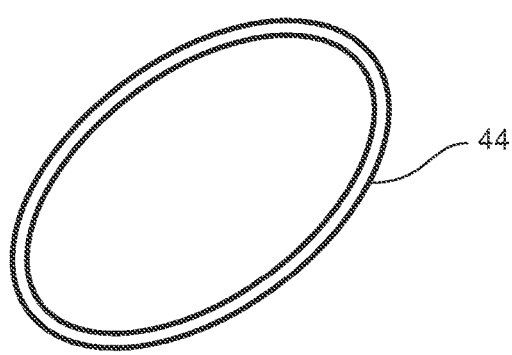
FIG. 10 is a perspective view of an O-ring.

The inverted cornea 32 is placed on the convex projection 18 and forms a fluid seal between the fluid chamber 24 of the top portion 12 and the interior recessed opening 14 of the base portion 10. Only the endothelial surface 34 of the inverted cornea 32 is exposed to the fluid chamber 24. A groove 42 may be formed on a lower exterior circumferential surface of the top portion 12. An O-ring 44 (FIG. 10) may be disposed in the groove 42. The O-ring 44 may provide a friction fit between the top portion 12 and a side surface 46 of the opening 14 in the base portion 10. O-ring 44 stabilizes top portion 12 on base portion 10 and thereby contributes to the fluid seal formed by the inverted cornea 32. In addition, in the event any fluid leaks past cornea 32, O-ring 44 contains the leaked fluid in base portion 10.

A plurality of the top portions 12 may be provided. The opening 22 in each top portion 12 may have a different diameter. The differing diameters of the openings 22 may be used to accommodate different size corneas, for example, corneas from different species of animals. For a guinea pig cornea, the diameter of opening 22 may be, for example, 7 mm. For a human cornea, the diameter of opening 22 may be, for example, 11.5 mm. The diameter of opening 22 is set to be equal to the diameter of the cornea. The cornea may be slightly stretched to account for minor differences in the diameter of the cornea in the vertical and horizontal direction. Slightly stretching the cornea may be advantageous because it facilitates degradation of the CEC attachment sites by enzymes.

The height of the convex projection 18 may vary with the height of the cornea as measured from the cornea center to the cornea periphery. This adjustment is necessary because corneas from different species cover different percentages of the eye globe. For example, porcine corneas occupy a smaller percentage of the porcine eye globe compared to the percentage that a guinea pig cornea covers a guinea pig eye globe. In other words, the periphery of the guinea pig cornea extends further back toward the eye socket than the periphery of the porcine eye globe.

The base and top portions 10, 12 are configured for printing by a 3D printer. The 3D printable design is particularly advantageous in that the same basic design of the isolation device 8 can be utilized for different species, with slight alterations in the diameter of opening 22 and the diameter and height of projection 18. These changes can be made in the computer-assisted drawing (CAD) file that defines each device component before export to a machine capable of 3D printing. Multiple copies of the isolation device 8 can be readily manufactured according to need. Isolation device 8 may be 3D printed using a material such as, for example, polylactic acid. Polylactic acid can be sterilized using low temperature processes such as alcohol immersion or ethylene oxide exposure. If high temperature sterilization methods such as autoclaving are desired, a 3D printer capable of printing with metallic material may be used to manufacture isolation device 8.

The method of using the isolation device 8 includes placing a cornea 32 with its endothelial side 34 up over the convex projection 18. The top portion 12 is mated with the base portion 10 such that the convex projection 18 extends into the opening 22. The endothelial layer 34 of the cornea 32 contacts the entire circumference of the opening 22. Only the endothelial layer 34 will be exposed to the fluid in the fluid chamber 24 of the top portion 12. Proteolytic enzymes that degrade CEC attachment sites, for example, trypsin and dispase, may be added to the fluid chamber 24. The fluid chamber 24 in top portion 12 functions as a chamber or container for containment of the enzymatic digestion solutions.

The total volume of the fluid chamber 24 is in a range of about 2 milliliters to about 12 milliliters, although larger volumes may be used. In one embodiment, the total volume of fluid chamber 24 is about 10 milliliters. The volume of enzymatic solution contained in chamber 24 may be in a range of about 2 milliliters to about 8.5 milliliters. When automated components are used, as discussed in detail below, the maximum volume of solution in the chamber 24 is the total volume of the chamber 24. Following incubation in the presence of the enzyme(s), CECs are easily released from the remaining cornea by repeated pipetting of enzymatic solution. The CECs may then be isolated from the suspension by centrifugation. The isolated CECs may then be grown in culture. For example, the isolated CECs may be grown for six days. The grown CECs may then be frozen.

Test Results

A. CEC Isolation-Two Pig Eyes. Feb. 5, 2015.

Setup:

Dispase II: Add 340 mg to 20 mL complete DMEM/F12 containing 10% FBS and 2× antibiotic/antimycotic. Place in 37 degree C. bath. Aliquot out 100 mL sterile PBS+a.a. for 1 day use. Add 1 mL a.a. to make a total of 2× a.a. Set out two 15 cm dishes, scalpel blade. Sterilize medium pointed scissors, non-serrated sharp narrow forceps, serrated narrow forceps. Sterilize cornea cell isolation devices in 70% ethanol and let dry. Coat T-75 flask with collagen IV. Use 394 ul collagen IV stock into 7.5 mL FBS.

Initial Dissection:

Working in a 15 cm dish containing enough PBS to keep tissues moist, dissect out the cornea plus 2-3 mm of surrounding sclera. It is convenient to use a scalpel for initial cut and scissors for remaining corneal removal.

Enzyme Digestion:

Lay cornea endothelium side up on device base. Push upper chamber of cornea cell isolation device into the lower base over cornea such that only the endothelium is exposed. Add 1 mL 0.25% pre-warmed trypsin to chamber. Place in incubator at 37 degrees C. for 5 minutes. Add 5 mL Dispase II to each corneal cell isolation device and cover with petri dish lid. Place in incubator at 37 degrees C. for 1 hour. After 1 hour incubation, pipette Dispase II solution repeatedly over endothelium surface to bring cells into suspension. Combine and transfer suspension to 15 mL conical tube. Pellet by centrifugation at 500×g for 10 minutes. Aspirate supernatant. Loosen pellet. Re-suspend in 20 mL Proulx medium+25 ug/mL+20 ul gentamycin.

B. CEC Isolation-Four Pig Eyes. Feb. 13, 2015.

Day 1-Corneal Isolation.

Setup:

Set out two 15 cm dishes, scalpel blade, sterile forceps, scissors.

Cornea Dissection:

Working in a 15 cm dish containing enough PBS to keep tissues moist, dissect out the cornea plus 2-3 mm of surrounding sclera. It is convenient to use a scalpel for initial cut and scissors for remaining corneal removal. Add to 20 mL complete DMEM/F12+1:1000 gentamycin in a 10 cm dish and leave o/n at 37 degrees C.

Day 2-CEC Isolation.

CEC Isolation Setup:

Sterilize 4 cornea cell isolation devices in 70% ethanol and let dry in cell culture hood. Dispase II: Add 680 mg to 40 mL complete DMEM/F12 containing 10% FBS and 2× antibiotic/antimycotic. Place in 37 degree C. water bath. Aliquot out 100 mL sterile PBS+a.a. for 1 day use. Add 1 mL a.a. to make a total of 2× a.a. Coat two T-75 flasks with collagen IV. Use 800 uL collagen IV stock into 15 mL PBS. Add 7.5 mL/flask and leave at 37 degrees C. for at least 1 hour.

Enzyme Digestion:

Lay cornea endothelium side up on device base. Snap upper chamber of cornea cell isolation device over cornea such that only the endothelium is exposed. Add 2 mL 0.25% pre-warmed trypsin to chambers. Place in incubator at 37 degrees C. for 5 minutes. Add 10 mL Dispase II solution to each corneal cell isolation device and cover with petri dish lid. Place in incubator at 37 degrees for 1 hour. After 1 hour incubation, pipette Dispase II solution repeatedly over endothelium surface to bring cells into suspension. Combine and transfer suspension to 15 mL conical tube. Pellet by centrifugation at 500×g for 10 minutes. Aspirate supernatant. Loosen pellet. Re-suspend in 40 mL Proulx medium+32 ul FGF at 25 ug/mL. Rinse collagen IV-coated flasks once with PBS. Add 20 mL cell suspension to each flask and place in 37 degree C. incubator.

Yield Calculation:

The isolated CECs were grown for six days in culture, and then divided to 30 vials for storage in liquid nitrogen. On Feb. 24, 2015, two vials from this batch were thawed and counted to be used in an experiment to compare two different cell growth medium formulations. Each vial was thawed and counted separately. The average number of live cells recovered was calculated to equal 810,000 cells per vial. Assuming each vial has 810,000 live cells, the total number is 30×810,000 or 24,000,000 CECs. Given that four porcine corneas were utilized, 6,000,000 CECs per porcine cornea may be obtained after six days of culture.

Embodiments of the Invention with Automation

The utility of the apparatus 8 may be enhanced with additional components. These components enable additional functions and features. One additional feature is automated fluid delivery so that enzymatic solutions can be delivered to the fluid chamber 24 in accordance with specific user-defined volumes and speeds. A second additional feature is uniform wash of the endothelial surface. Pressurized fluid is delivered to the endothelial surface through a "full cone" nozzle that results in high flow rates consistent in force over the entire endothelial area. A third additional feature is automated sample collection wherein cell isolates are collected in a conical centrifuge tube ready for further processing. A fourth additional feature is programmable process control. Precise control of incubation timing and fluid force is enabled by incorporating a programmable microcontroller (circuit board with minimal operating system) into the assembly.

Automated Fluid Delivery

With automated fluid delivery, addition of an enzymatic solution to the fluid chamber 24 is performed automatically with a pump or pumps. Typically, the enzymatic solution is Dispase II in DMEM/F12+10% FBS. After the enzymatic solution digests the endothelial surface, repeated manual pipetting of the solution onto the endothelial surface to bring the CECs into suspension is not required. All the process steps, from reagent addition to resuspension of the pelleted isolate into growth medium are achieved in a closed system. Tissues and cell suspensions remain within sealed enclosures and tubing during isolation steps. Closed system processing is generally required in clinical manufacturing to minimize the risk of microbial contamination of the finished product. Tissues and cell suspensions remain within sealed enclosures and tubing during isolation steps.

Figure 12:
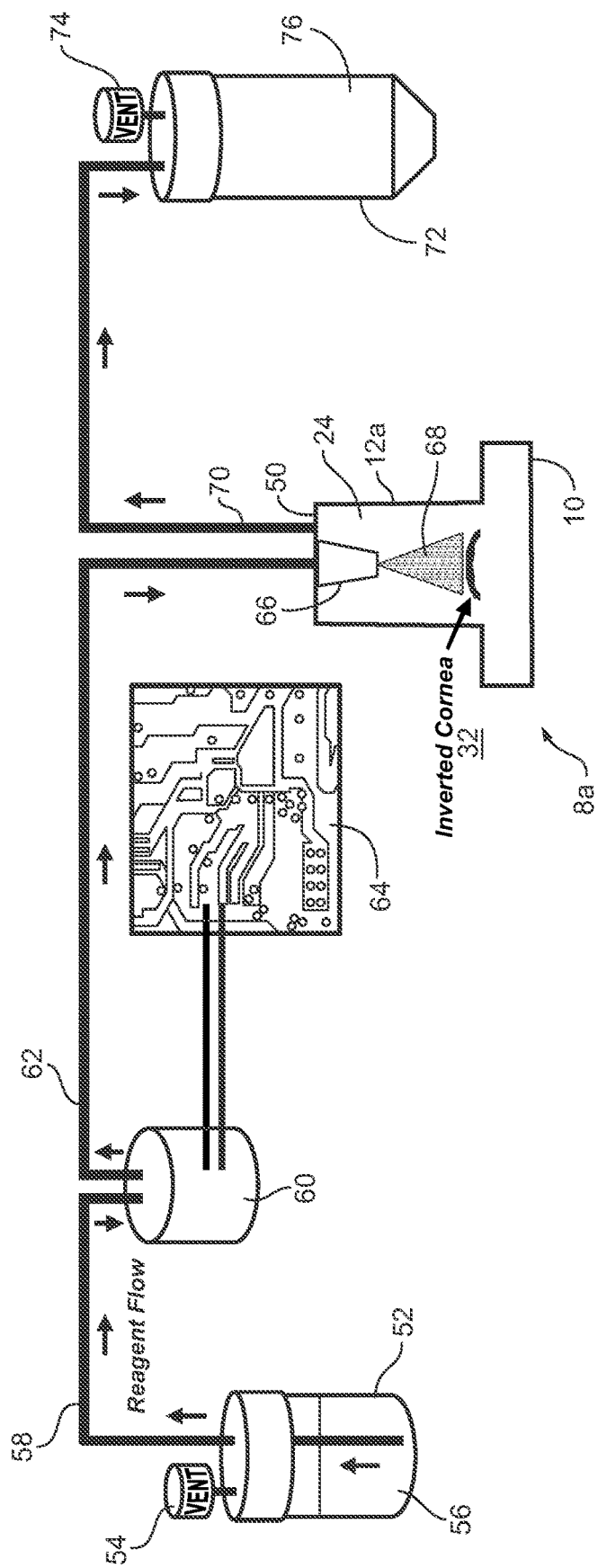
FIG. 12 is a schematic diagram of one embodiment of an automated apparatus for isolation of endothelial cells.
Figure 13:
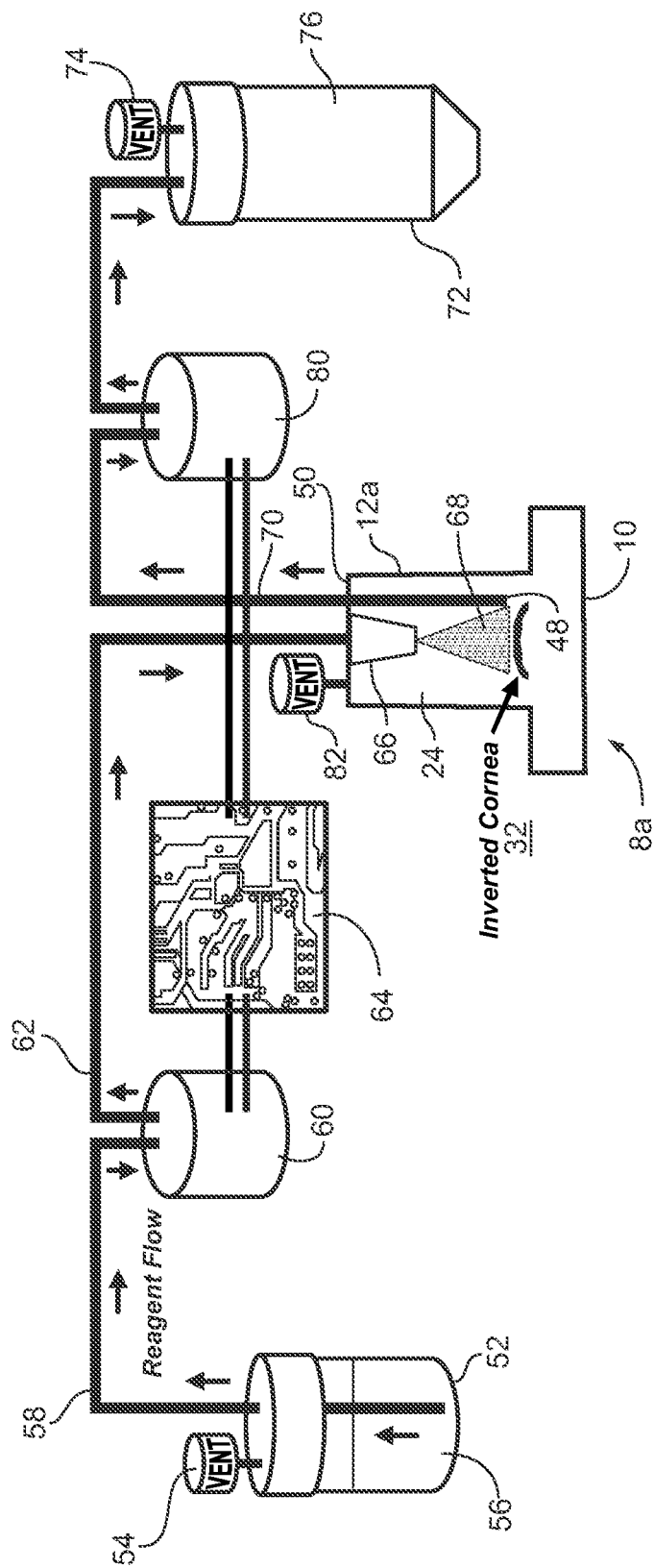
FIG. 13 is a schematic diagram of a second embodiment of an automated apparatus for isolation of endothelial cells.
Figure 14:
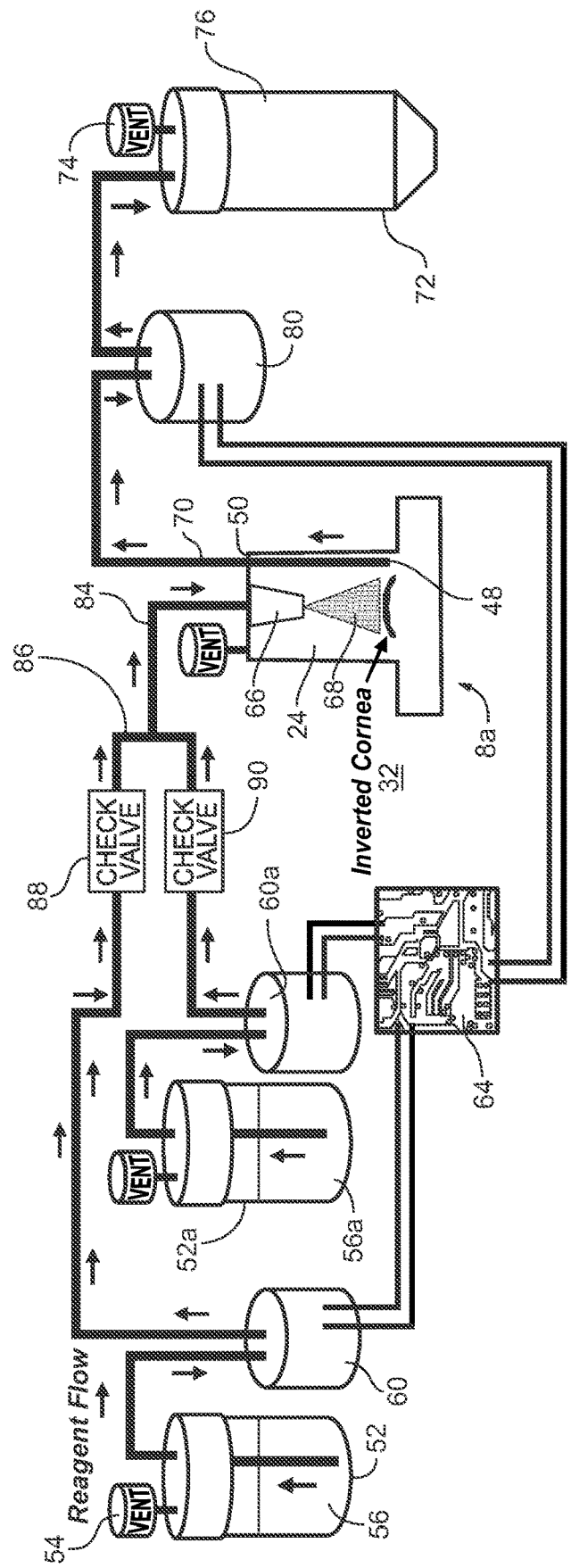
FIG. 14 is a schematic diagram of a third embodiment of an automated apparatus for isolation of endothelial cells.

FIGS. 12-14 are schematic diagrams of three exemplary embodiments of an automated assembly for isolation of endothelial cells.

Referring to FIG. 12, a reagent reservoir 52 contains reagent 56. Reagent 56 may be, for example, Dispase II in DMEM/F12+10% FBS. Reservoir 52 may have a volume of, for example, 10 milliliters. A vent 54 vents reservoir 52. Tubing 58 carries reagent from reservoir 52 to peristaltic pump 60. Tubing 62 carries reagent 56 from pump 60 to isolation assembly 8a. Tubing 70 carries reagent 56 with endothelial cells 34 from isolation assembly 8a to collection tube 72. Collection tube 72 is preferably a conical centrifuge tube. Tube 72 may have a volume of, for example, 50 milliliters. Isolation assembly 8a is similar to isolation assembly 8 shown in FIGS. 1-7 and 11.

Isolation assembly 8a differs from assembly 8 by the addition of a closed lid 50 on top portion 12a. Lid 50 has openings for tubing 62 and 70. A full cone spray nozzle 66 (FIGS. 15A and B) is fixed to the underside of lid 50. Full cone spray nozzle 66 produces a spray pattern 78 shown in an angled side view in FIG. 15A and in a bottom view in FIG. 15B.

Reagent fluid 56 is moved from reagent reservoir 52 through fluid chamber 24 in isolation assembly 8a by peristaltic pump 60. Pump 60 may operate at 12 volts or 24 volts. Pump 60 may have a maximum flow rate of 200 to 500 milliliters per minute, for example. Pump 60 generates directional flow through rhythmic compressions of fluid-filled tubing. Peristaltic pumps are designed to maintain the separation of sterile fluids within the tubing from mechanical pump components. The reservoir 52 is sterilely vented with vent 54 to release negative pressure that would otherwise accumulate as fluid 56 is pumped out of the reservoir. An electronic microcontroller 64 switches pump 60 on and off, controls the speed of reagent flow while the pump 60 is on, and determines the length of time the pump 60 will be in the "on" or "off" state during each step of the process.

Corneal tissue 32 is seated in the base portion 10 of the isolation device 8a with the CECs 34 facing upward into chamber 24. Corneal tissue 32 may be incubated in enzymatic solutions at user-defined time periods. After the chamber 24 is filled with enzyme solution, the pump 60 may be placed in the "off" state by the microcontroller 64. The length of time that the pump 60 is in the "off" state can be adjusted to obtain maximal CEC yield.

To detach CECs 34 from the remaining cornea, the microcontroller 64 places the pump 60 in the "on" state and passes reagent 56 through a full cone nozzle 66 at a relatively high flow rate. The resulting high-pressure fluid flow facilitates CEC release from underlying corneal tissue and brings the cells into suspension. The detached, suspended CECs 34 are forced through a final tubing segment 70 that connects the isolation device 8a to a vented collection tube 72. The tube vent 74 releases positive pressure, allowing forward movement of the cell suspension and deposition into the collection tube 72. The collection tube 72 is preferably of a type that may be directly mounted into a centrifuge.

Referring now to FIG. 13, the assembly of FIG. 13 operates under the same general principles as the embodiment of FIG. 12, but incorporates an additional peristaltic pump 80 situated between the isolation device 8a and the collection tube 72. Microcontroller 64 can operate both pumps 60, 80 simultaneously. The pump 80 provides additional control of fluid 56 through the assembly. The additional pump 80 introduces a compression point in the tubing 70 that connects the isolation device 8a to the collection tube 72. While pump 80 is in the "off" state therefore, fluid movement within the tubing 70 is prevented. This arrangement blocks possible fluid spillage from the isolation device 8a to the collection tube 72, or from the collection tube 72 back into the isolation device 8a.

In FIG. 13, a sterile vent 82 is incorporated within the isolation device 8a. Therefore, when the reagent reservoir pump 60 is in the "off" state and the pump 80 is in the "on" state, the fluid chamber 24 of the isolation device 8a can be drained at a specific stage in the process. Draining the contents of chamber 24 may be desirable in cases where the enzymatic reagents that are used are costly. For example, with the addition of pump 80, no additional enzyme solution would be required to carry detached CECs 34 out of the chamber 24 and into the collection tube 72, in contrast to the embodiment of FIG. 12. In FIG. 13, the end 48 of tubing 70 extends into the fluid chamber 24 and terminates adjacent the convex projection 18 and inverted cornea 32.

The ability to drain the chamber 24 also enables repeated rinsing of corneal tissue after CECs 34 are suspended by high pressure flow from the full cone nozzle 66. For example, with the reservoir pump 60 off and the pump 80 on, re-suspended cell suspension is delivered to the collection tube 72. If the pump 80 is then turned off and the reagent pump 60 is turned on, fresh solution is delivered to the tissue sample. The rinse solution can in turn be removed and transferred to the collection tube 72 by turning the pump 80 back on while holding the reservoir pump 60 in the off state. A rinse sequence can be repeated multiple times to achieve maximal transfer of residual CECs 34 from the chamber 24 to the collection tube 72.

Referring to FIG. 14, a third embodiment of the CEC isolation assembly enables the use of two distinct reagent fluids 56, 56a during the same operation run. Importantly, the assembly still operates as a closed system. No components of the system must be removed or opened to allow the in-process addition of the second reagent fluid 56a. The pump 80 as described with reference to FIG. 13 is included in the embodiment of FIG. 14.

Incorporation of a second reagent fluid 56a is achieved by adding a second reagent reservoir 52a and pump 60a to the assembly. A single microcontroller 64 is capable of independently and simultaneously operating all three pumps 60, 60a and 80. Reagent flow from each of the two reservoirs 52, 52a is driven by a corresponding pump 60, 60a (i.e., each reservoir is paired with a dedicated, independently operating pump). Fluid flow from the reservoirs 52, 52a follows a tubing path that converges to a single line 84 via a "Y"-type tubing connector 86 before entering the isolation device 8a.

To ensure delivery of one reagent at a time to the chamber 24, check valves 88, 90 are incorporated into the tubing path just prior to the position of the "Y" connector 86. Check valves 88, 90 are only open to allow fluid flow when fluid pressure is exerted on the respective valve 88, 90. Sequential delivery of two separate reagents 56, 56a is achieved in the following manner Pump 60 is switched on by the microcontroller 64, while pump 60a is maintained in the "off" state. As pressure builds in the tubing path maintained by pump 60, the check valve 88 within this path opens. The tubing path operated by pump 60a remains closed since there is no pressure accumulation to open the check valve 90 in the corresponding tubing path.

The microcontroller 64 can be programmed to deliver the first reagent 56 for a set period of time. When the specified time to stop reagent delivery is reached, pump 60 is set to the "off" state, fluidic pressure in the tubing path of pump 60 drops, and the check valve 88 for this path closes. To deliver the second reagent 56a to the chamber 24 of the isolation device 8a, pump 60a is set to "on", while pump 60 is maintained in the "off" state. Pressure within the tubing path for pump 60a increases until the check valve 90 in this path is open. Reagent 56a will now flow into the chamber 24 of the isolation device 8a without prior mixing with reagent 56.

Uniform Wash of the Endothelial Surface

Figure 15A:
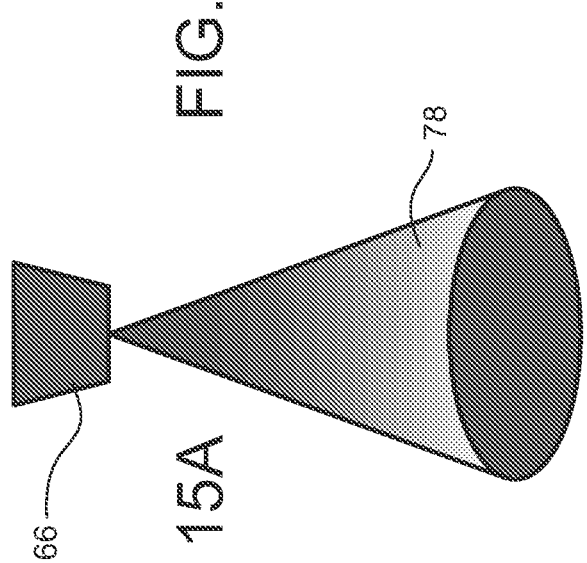
FIGS. 15A and B are schematic views of a full cone spray nozzle and spray pattern.
Figure 15B:
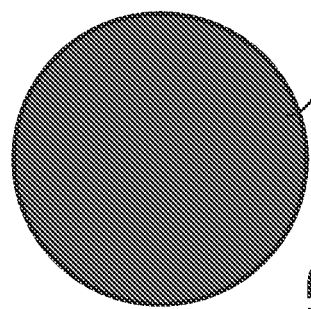
Figure 16A:
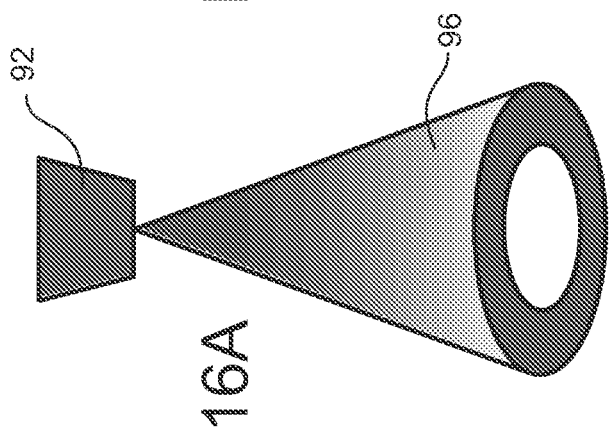
FIGS. 16A and B are schematic views of a hollow cone spray nozzle and spray pattern.
Figure 16B:
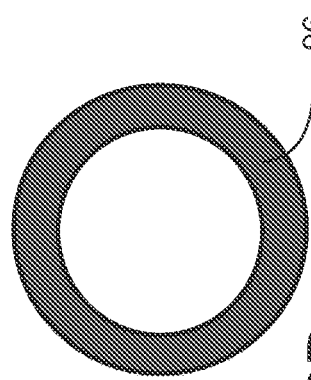
Figure 17A:
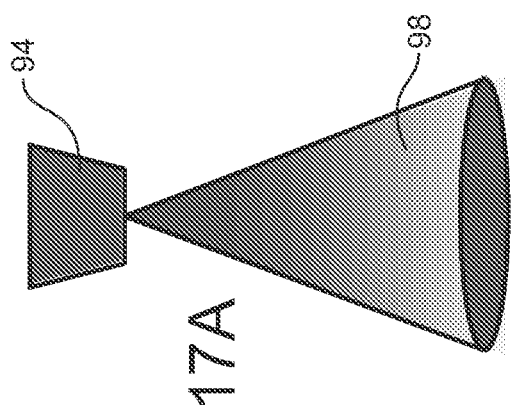
FIGS. 17A and B are schematic views of a flat fan spray nozzle and spray pattern.
Figure 17B:

Enzymatic solutions and wash solutions are passed through a "full cone" spray nozzle 66. FIGS. 15A and B are schematic views of a full cone spray nozzle 66 and spray pattern 78. Spray pattern 78 is shown in angled side view in FIG. 15A and in bottom view in FIG. 15B. By way of contrast, FIGS. 16A and B are schematic views of a hollow cone spray nozzle 92 and spray pattern 96 and FIGS. 17A and B are schematic views of a flat fan spray nozzle 94 and spray pattern 98. Spray patterns 96, 98 are shown in angled side views in FIGS. 16A and 17A, respectively, and in bottom views in FIGS. 16B and 17B, respectively. The full cone configuration of FIGS. 15A and B emits a relatively even distribution of flow over the endothelial surface, compared to the hollow cone nozzle 92 (FIGS. 16A and B) or flat fan nozzle 94 (FIGS. 17A and B) configuration.

Automated Sample Collection

Fluids are moved through the processing assembly, terminating with sample collection in a collection or centrifuge tube 72. After the isolated CECs are dispensed in the centrifuge tube 72, the cells can be pelleted by centrifugation, re-suspended in nutrient growth medium and seeded to a cell culture vessel for in vitro expansion of cell number.

Programmable Process Control

Operation of the peristaltic pump(s) utilized in the automated process is determined by signals received from a microcontroller 64, which is a circuit board with a rudimentary operating system. Various microcontrollers are available on the market. In one embodiment, the microcontroller 64 may be a Raspberry Pi brand of microcontroller.

The Raspberry Pi microcontroller can interpret and implement instructions from the simple computer programming language "Python". As an example, Python may be used to control the following process sequence of a single pump 60 in the embodiment of FIG. 12:

(1) Start the flow of enzyme solution 56 from the reagent reservoir 52.
(2) Fill the chamber 24 of the CEC isolation device 8a.
(3) Stop the flow to allow sufficient digestion of CEC-to-DM (Descemet's Membrane) attachment sites (for example 1 hr).
(4) Pulse a high speed (high pressure) flow of additional solution 56 over the endothelial surface to loosen CECs 34 and bring them into suspension (for example, 20 pulses lasting 3 seconds each). Note from FIG. 12 that as flow continues above the volume that can be contained by the fluid chamber 24, excess volume is dispensed into the collection tube 72. Solution 56 from the reagent reservoir 52 will be fed into the system until CECs 34 are dispensed to the collection tube 72.

Also note that varying enzyme digestion times (for example, 1 hour, 1.5 hours, 2 hours) can be programmed into the microcontroller 64. Likewise, the number and pressure of fluid pulses used to free cells from Descemet's Membrane 38 (FIG. 9) can also be varied according to instructions written into Python code. A simplified example of Python code capable of controlling the behavior of a peristaltic pump 60 is shown below. When the below code is executed, the microcontroller 64 will turn on a peristaltic pump 60 (denoted as "motor" in the code) at 100% power. The pump 60 will continue to operate for 30 seconds and then will turn off.

Code:

```
import RPi.GPIO as GPIO
GPIO.setwarnings (False)
GPIO.setmode(GPIO.BOARD)
import time
GPIO.setup(32,GPIO.OUT)
GPIO.setup(36,GPIO.OUT)
GPIO.setup(40,GPIO.OUT)
PWM=GPIO.PWM(32,60)              #GPIO pin 32 set for Pulse Width Modulation.
                                 Second number in parentheses is Hz.
IN1=36                           #GPIO 36=IN1 on motor controller
IN2=40                           #GPIO 40=IN2 on motor controller
print ("Motor On at 100%)
PWM.start(100)                   #number in parentheses=duty cycle. Valid
                                 entries are >=0 (slowest) and <=0 (fastest).
GPIO.output(IN1,GPIO.HIGH)
GPIO.output(IN2,GPIO.LOW)
time.sleep (30)
PWM.stop( )                      #Stop PWM output.
Print ("Motor Off")
GPIO.cleanup( )
```

Embodiments of the invention have been described to explain the nature of the invention. Those skilled in the art may make changes in the details, materials, steps and arrangement of the described embodiments within the principle and scope of the invention, as expressed in the appended claims.

What is claimed is:

1. An apparatus for isolating corneal endothelial cells (CECs), comprising:
   a base portion having an interior recessed opening with a bottom surface;
   a convex projection centrally located on the bottom surface;
   an inverted cornea disposed on the convex projection with an endothelial layer of the cornea facing upward; and
   a top portion configured to mate with the base portion, the top portion including a fluid chamber with a lower surface, the lower surface having a central opening therein in which the convex projection projects when the top portion is mated with the base portion;
   wherein the lower surface of the top portion extends from and angles up and away from the opening therein and joins a side wall of the top portion, and the inverted cornea forms a fluid seal between the fluid chamber of the top portion and the interior recessed opening of the base portion and further wherein only an endothelial surface of the inverted cornea is exposed to the fluid chamber.

2. The apparatus of claim 1, wherein an angle between the lower surface of the top portion and a horizontal is in a range of 30 degrees to 70 degrees.

3. The apparatus of claim 2, wherein the angle is in a range of about 40 degrees to about 60 degrees.

4. The apparatus of claim 1, further comprising a groove formed on a lower exterior circumferential surface of the top portion and an O-ring disposed in the groove, wherein the O-ring provides a friction fit between the top portion and the base portion.

5. The apparatus of claim 1, further comprising a plurality of the top portions wherein the opening in each top portion has a different diameter.

6. The apparatus of claim 1, wherein the apparatus is configured for printing by a 3D printer.

7. The apparatus of claim 1, wherein the CECs are mammalian CECs.

8. A method for isolating corneal endothelial cells (CECs), comprising:
   providing the apparatus of claim 1 wherein the inverted cornea is a mammalian cornea;
   placing the cornea with its endothelial side up over the convex projection; and
   mating the top portion with the base portion such that the convex projection extends into the opening and an endothelial layer of the cornea contacts an entire circumference of the opening wherein only the endothelial layer is exposed to the fluid chamber of the top portion.

9. The method of claim 8, further comprising adding trypsin to the fluid chamber.

10. The method of claim 8, further comprising digesting proteins in a Descemet's Membrane of the cornea by adding dispase to the fluid chamber.

11. The method of claim 8, wherein the step of placing the cornea includes slightly stretching the cornea with its endothelial side up over the convex projection.

12. The method of claim 9, further comprising, after the step of adding trypsin, digesting proteins in a Descemet's Membrane of the cornea by adding dispase to the fluid chamber.

13. The method of claim 10, further comprising repeatedly pipetting the dispase over the endothelial layer to bring the CECs into a suspension.

14. The method of claim 13, further comprising isolating the CECs from the suspension by centrifugation.

15. The method of claim 14, further comprising growing the isolated CECs in culture.

16. The method of claim 15, further comprising growing the CECs for six days.

17. The method of claim 16, further comprising freezing the grown CECs.

18. An assembly, comprising:
   a reservoir containing a reagent;
   a peristaltic pump fluidly connected to the reservoir with tubing;
   a microcontroller connected to and in control of the peristaltic pump;
   the apparatus of claim 1 wherein the fluid chamber is connected to the peristaltic pump with the tubing;
   a lid that closes the top portion;
   a spray nozzle fixed to the lid and configured to receive the reagent from the tubing and spray the reagent in the fluid chamber onto the inverted cornea;
   a collection tube for collecting the reagent and endothelial cells from the fluid chamber; and
   a second tubing that connects the fluid chamber to the collection tube.

19. The assembly of claim 18, wherein the spray nozzle is a full cone spray nozzle.

20. The assembly of claim 18, further comprising a second peristaltic pump connected to and controlled by the microcontroller and interposed in the second tubing between the fluid chamber and the collection tube.

21. The assembly of claim 20, wherein the second tubing extends into the fluid chamber and terminates adjacent to the inverted cornea.

22. An assembly, comprising:
   a first reservoir containing a first reagent;
   a first peristaltic pump fluidly connected to the first reservoir with a first tubing;
   a second reservoir containing a second reagent;
   a second peristaltic pump fluidly connected to the second reservoir with a second tubing;
   a microcontroller connected to and in control of the first and second peristaltic pumps;
   the apparatus of claim 1 wherein the fluid chamber is connected to the first and second tubing by a Y-connection tubing;
   a check valve in each of the first and second tubing upstream from the Y-connection tubing;
   a lid that closes the top portion;
   a spray nozzle fixed to the lid and configured to receive the first and second reagents from the Y-connection tubing and spray the first and second reagents in the fluid chamber onto the inverted cornea;
   a collection tube for collecting the first and second reagents and endothelial cells from the fluid chamber;
   a third tubing that connects the fluid chamber to the collection tube; and
   a third peristaltic pump connected to and controlled by the microcontroller and interposed in the third tubing between the fluid chamber and the collection tube.

23. The assembly of claim 22, wherein the spray nozzle is a full cone spray nozzle.

24. The assembly of claim 22, wherein the third tubing extends into the fluid chamber and terminates adjacent to the inverted cornea.

25. An apparatus for isolating corneal endothelial cells (CECs), comprising:
  a base portion having an interior recessed opening with a bottom surface;
  a convex projection centrally located on the bottom surface;
  an inverted cornea disposed on the convex projection with an endothelial layer of the cornea facing upward;
  a top portion configured to mate with the base portion, the top portion including a fluid chamber with a lower surface, the lower surface having a central opening therein in which the convex projection projects when the top portion is mated with the base portion; and
  a groove formed on a lower exterior circumferential surface of the top portion and an O-ring disposed in the groove, wherein the O-ring provides a friction fit between the top portion and the base portion;
  wherein the lower surface of the top portion extends from and angles up and away from the opening therein and joins a side wall of the top portion, and the inverted cornea forms a fluid seal between the fluid chamber of the top portion and the interior recessed opening of the base portion and further wherein only the endothelial layer of the inverted cornea is exposed to the fluid chamber.

26. An assembly for isolating corneal endothelial cells (CECs), comprising:
  an isolation apparatus including
    a base portion having an interior recessed opening with a bottom surface;
    a convex projection centrally located on the bottom surface;
    an inverted cornea disposed on the convex projection with an endothelial layer of the cornea facing upward;
    a top portion configured to mate with the base portion, the top portion including a fluid chamber with a lower surface, the lower surface having a central opening therein in which the convex projection projects when the top portion is mated with the base portion; and
    a groove formed on a lower exterior circumferential surface of the top portion and an O-ring disposed in the groove, wherein the O-ring provides a friction fit between the top portion and the base portion;
    wherein the lower surface of the top portion extends from and angles up and away from the opening therein and joins a side wall of the top portion, and the inverted cornea forms a fluid seal between the fluid chamber of the top portion and the interior recessed opening of the base portion and further wherein only the endothelial layer of the inverted cornea is exposed to the fluid chamber;
  a reservoir containing a reagent;
  a peristaltic pump fluidly connected to the reservoir with tubing wherein the fluid chamber is connected to the peristaltic pump with the tubing;
  a microcontroller connected to and in control of the peristaltic pump;
  a lid that closes the top portion;
  a spray nozzle fixed to the lid and configured to receive the reagent from the tubing and spray the reagent in the fluid chamber onto the inverted cornea;
  a collection tube for collecting the reagent and endothelial cells from the fluid chamber;
  a second tubing that connects the fluid chamber to the collection tube; and
  a second peristaltic pump connected to and controlled by the microcontroller and interposed in the second tubing between the fluid chamber and the collection tube.

* * * * *

UNITED STATES PATENT AND TRADEMARK OFFICE
CERTIFICATE OF CORRECTION

PATENT NO. : 10,443,032 B2  
APPLICATION NO. : 16/060078  
DATED : October 15, 2019  
INVENTOR(S) : Robert Haggins, Jr. et al.

Page 1 of 1

It is certified that error appears in the above-identified patent and that said Letters Patent is hereby corrected as shown below:

On the Title Page

Delete 10 occurrences of the upper case letter M superimposed randomly on the left hand side of the page.

Signed and Sealed this  
Tenth Day of December, 2019

Andrei Iancu  
*Director of the United States Patent and Trademark Office*